(12) United States Patent
Sarvazyan et al.

(10) Patent No.: US 8,388,518 B2
(45) Date of Patent: Mar. 5, 2013

(54) SIMPLIFIED HANDGRIP FOR ASSESSMENT OF COLONOSCOPE MANIPULATION

(75) Inventors: Armen P. Sarvazyan, Lambertville, NJ (US); Aleksandr Pasechnik, Manalapan, NJ (US); Sergey Tsyuryupa, Westampton, PA (US); Vladimir Egorov, Princeton, NJ (US)

(73) Assignee: Artann Laboratories Inc., Trenton, NJ (US)

( * ) Notice: Subject to any disclaimer, the term of this patent is extended or adjusted under 35 U.S.C. 154(b) by 29 days.

(21) Appl. No.: 13/267,838

(22) Filed: Oct. 6, 2011

(65) Prior Publication Data

US 2012/0029286 A1 Feb. 2, 2012

Related U.S. Application Data

(63) Continuation-in-part of application No. 12/558,737, filed on Sep. 14, 2009, now Pat. No. 8,033,991.

(51) Int. Cl.
*A61B 1/00* (2006.01)
(52) U.S. Cl. ........................ 600/131; 600/117; 600/101
(58) Field of Classification Search ................ 600/101, 600/131, 117; 606/1; 434/262
See application file for complete search history.

(56) References Cited

U.S. PATENT DOCUMENTS

| | | | | |
|---|---|---|---|---|
| 5,623,582 | A * | 4/1997 | Rosenberg | 700/264 |
| 6,038,488 | A * | 3/2000 | Barnes et al. | 700/161 |
| 6,726,675 | B1 * | 4/2004 | Beyar | 604/510 |
| 6,981,945 | B1 * | 1/2006 | Sarvazyan et al. | 600/131 |
| 8,333,689 | B2 * | 12/2012 | Okamoto et al. | 600/102 |
| 2006/0161045 | A1 * | 7/2006 | Merril et al. | 600/117 |
| 2006/0217687 | A1 * | 9/2006 | Bakos et al. | 606/1 |
| 2008/0146875 | A1 * | 6/2008 | Noguchi et al. | 600/117 |
| 2011/0065989 | A1 * | 3/2011 | Sarvazyan et al. | 600/117 |
| 2011/0065991 | A1 * | 3/2011 | Sarvazyan et al. | 600/131 |
| 2011/0208000 | A1 * | 8/2011 | Honda et al. | 600/118 |

OTHER PUBLICATIONS

Mosse et al., "Device for measuring the forces exerted on the shaft of an endoscope during colonoscopy", Mar. 1998, Medical & Biological Engineering and Computing, pp. 186-190.*

* cited by examiner

*Primary Examiner* — John P Leubecker
(74) *Attorney, Agent, or Firm* — Boris Leschinsky

(57) ABSTRACT

A handgrip for a colonoscope shaft is equipped with a novel compact multifunction force and torque sensor allowing for a comprehensive characterization of colonoscope manipulation during a colonoscopy procedure. A two-part hinge design of the handgrip in combination with the multifunction sensor provides for a light weight design in a compact package making using the handgrip convenient and natural. An electronic unit is provided to receive the sensor data wirelessly and calculate a variety of motion parameters guiding a medical practitioner during the procedure and aimed at making colonoscopy safer and less painful.

13 Claims, 8 Drawing Sheets

SIMPLIFIED HANDGRIP FOR ASSESSMENT OF COLONOSCOPE MANIPULATION

REFERENCES TO RELATED APPLICATIONS

This application claims a priority benefit and is a continuation-in-part of U.S. patent application Ser. No. 12/558,737 filed 14 Sep. 2009, now U.S. Pat. No. 8,033,991 entitled "A HANDGRIP FOR ASSESSMENT OF COLONOSCOPE MANIPULATION", which is incorporated herein in its entirety by reference.

REFERENCE TO GOVERNMENT-SPONSORED RESEARCH

This invention was made with the U.S. government support under SBIR grant No. R44 DK068936-02entitled "Colonoscope Force Monitor" and awarded by the National Institute of Health, National Institute of Diabetes and Digestive and Kidney Diseases. The government has certain rights in this invention.

BACKGROUND OF THE INVENTION

The present invention relates generally to devices aiding in insertion of steerable catheters and scopes. More particularly, the invention describes a handgrip positioned over the shaft of a scope, such as a colonoscope, and configured for measuring and recording of colonoscope manipulation forces, torques, and accelerations.

In many cases, it has been desirable to examine internal organs, passages, and the like of the human body for the purposes of diagnosis, biopsy, and therapeutic interventions. One method of examining the internal organs of the patient without major surgery is to insert a remote sensing device such as an endoscope into the body through a natural body orifice such as a colon or a specially prepared surgical opening.

The primary area of application of the invention is for the use with a colonoscope, but other devices can also be used with the handgrip of the invention. Therefore, the word "colonoscope" is used throughout this description to broadly include various types of direct vision and fiberoptic endoscopes, fiberscopes, arthoscopes, enteroscopes, laparoscopes, and other steerable and deflectable catheters, guide wires, cannulaes and tubes designed to be inserted into blood vessels, tight tissue openings, and curved passages.

Although useful for industrial applications, the preferred area of use for the device of the present invention is in medicine, and more particularly in colonoscopy. Colonoscopy is the preferred method to screen for colorectal cancer, a disease that afflicts over 100,000 patients each year in the U.S. Several million colonoscopies are performed each year in U.S. hospitals and ambulatory surgery centers. Colonoscopy requires a physician to inspect the colonic mucosal surface by advancing the colonoscope through a series of stationary and movable colonic loops using linear and rotational manipulations.

A common objective during the procedure is the optimal maneuvering of the inspection end (distal end) of the scope and positioning it in proximity to the area of interest. This maneuvering is performed by a trained operator who uses a combination of visual and tactile feedback to coordinate the maneuvers through the twists and turns found in the colon. The operator subjectively senses the resistance to the maneuvers by the "feel" of the instrument and anticipates the amount of force and torque necessary to advance the colonoscope shaft forward. The application of force to the colon and its anatomic attachments can be painful. Particularly undesirable is the frequent occurrence of excessive contact pressure on the internal tissue, which can result in pain and, in rare cases, in colon perforation. Sedation and analgesia is frequently required to make the procedure comfortable. Preliminary studies demonstrate that a significant variation between operators exists in the level of applied push/pull forces during the examination procedure, and that these forces can be excessive. Operator training programs are designed to reduce the variation in technique. The need therefore exists to provide a device allowing for an effective, low-cost method of defining best practices, and to implement these practices as a part of medical record keeping, training, ongoing education, and quality assurance.

Useful designs of a handgrip for a colonoscope with force and torque measurement capability are described in U.S. Pat. Nos. 6,981,945 and 8,033,991 by the same inventors incorporated herein in its entirety by reference. The disclosed handgrips are capable of measuring and presenting to the operator the axial and radial plane forces, torques, and accelerations applied by the operator during the manipulation of the colonoscope. Despite their comprehensive functional performance, these handgrips include complex power-driven mechanisms allowing engaging and disengaging from the colonoscope shaft for repositioning. As a result, they are fairly large and heavy. Operating these handgrips is not as convenient as it may be should these devices be smaller and lighter.

In addition to the excessive weight and size, the prior art devices were configured for engaging and disengaging with the colonoscope shaft by pushing a button which activated a motorized engaging mechanism. Such method of operating the device is inconvenient and requires operator training as it steps away from an intuitive motion of gripping the colonoscope by hand during a conventional procedure.

The need exists therefore for a handgrip for the colonoscope shaft that allows easy repositioning while designed as a simple and intuitive to operate, light weight and small in size.

SUMMARY OF THE INVENTION

Accordingly, it is an object of the present invention to overcome these and other drawbacks of the prior art by providing a novel light weight and small handgrip for a colonoscope that measures, displays, and records various parameters associated with colonoscope maneuvering during a colonoscopy procedure. The parameters may include axial force, lateral force and torque applied to the colonoscope shaft, linear and rotational accelerations of the shaft, and position tracking of the handgrip relative to the shaft.

It is a further object of the present invention to provide a handgrip for the assessment of colonoscope manipulation which can be easily used with a variety of commercially available colonoscope instruments.

It is another object of the present invention to provide a handgrip adapted for simple and natural grip, release, and repositioning along the colonoscope shaft during colonoscope insertion and removal so that the handgrip location can be changed by the operator depending on clinical necessity.

It is yet a further object of the present invention to provide a handgrip which can be used multiple times and can withstand disinfection and sterilization by all commonly used methods without loss of the sensitivity of its measuring components.

The handgrip of the invention consists of one or in some embodiments two or more multifunction force/torque sensors positioned within a handgrip which in turn is designed as a hinge with two handles extending therefrom. The presence of two or more sensors allows correcting the force and torque signals for possible misalignments when manipulating the colonoscope shaft. The sensors may be located between the handles so that the act of bringing the handles together causes engaging of the handgrip with the colonoscope shaft through compressing of the sensors against the colonoscope shaft. The handgrip of the invention provides a substantial mechanical advantage due to the length of the handles being greater than the distance between the sensor and the hinge. The force and torque measuring sensors are configured for measuring and transmitting the gripping force as well as the axial forces, lateral forces, and torques applied by the operator. The colonoscope manipulation data is acquired from the sensors and preprocessed before wireless transmission to the personal computer or hospital electronic data storage system. The data can then be stored or displayed during the procedure or reviewed afterwards.

In order to place the handgrip of the invention over the colonoscope shaft, provisions are made to allow the two handles of the handgrip to separate and reconnect at the hinge. Alternatively, the colonoscope shaft can be passed through the opening in a single-body handgrip prior to the procedure and removed thereafter.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE PREFERRED EMBODIMENT OF THE INVENTION

Figure 1:
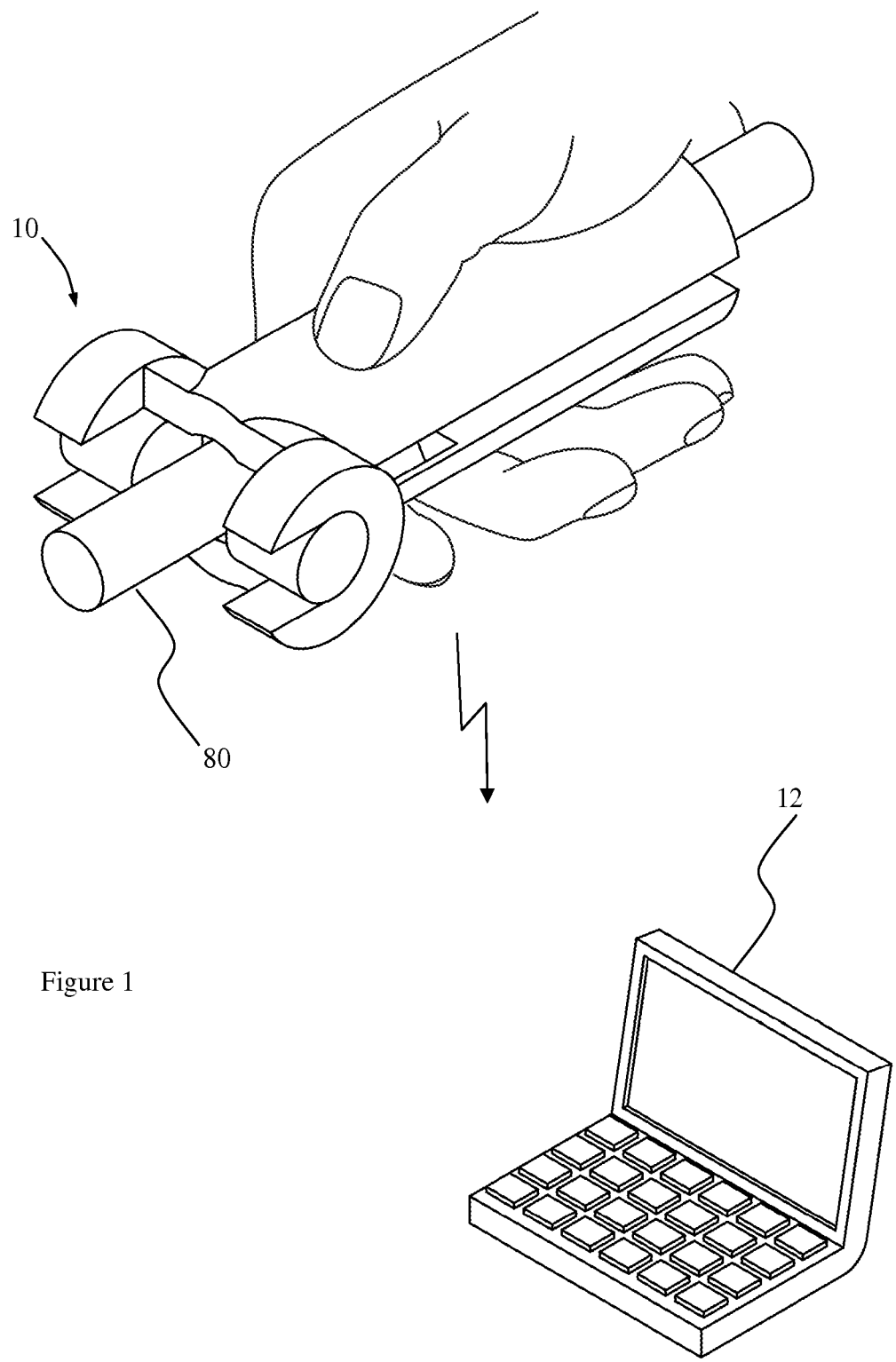
FIG. 1 is a general view of the handgrip of the invention positioned over the colonoscope shaft including a remote data storage and display system.

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Push, pull, and torque forces are applied to the colonoscope shaft during the colonoscopy procedure to advance it through the colon. Depending on a specific anatomy, the force applied against the wall of the colon can be substantial. The magnitude of the applied forces accounts for the two most important limitations of colonoscopy: pain and colonic perforation. Importantly, knowing only the force and toque applied to the colonoscope shaft is not sufficient to describe the procedure accurately. A comprehensive characterization of the procedure requires knowing the applied forces and torques as well as the resulting motion of the colonoscope shaft. The present invention is aimed to provide for such a comprehensive characterization as described below.

A general view of the invention is shown in FIG. 1. The handgrip 10 is shown placed around the colonoscope shaft 80. Note that only a small portion of the shaft 80 is shown on the drawing in the vicinity of the grip area for the operator holding the device. The handgrip 10 is equipped with force/torque, acceleration, and displacement sensors as will be described in more detail below. In embodiments, the data from the handgrip sensors is transmitted wirelessly to the data storage and display system such as computer 12 for data processing and recording. That transmission can be done using a number of known wireless protocols for example Bluetooth. As can be well appreciated by those skilled in the art, a wired transmission of data from the handgrip 10 to the computer 12 is also possible and falls within the scope of the invention. The wireless handgrip 10 has an advantage of providing maximal manipulation freedom for the operator.

In other embodiments (not shown in the drawings), the data from the handgrip sensors may be displayed on the handgrip itself or sent directly to the colonoscope image display apparatus. This data may be integrated on the colonoscope display together with real-time colonoscope camera video to provide a quantitative measure of the applied forces and dynamic response of the tissue. This configuration may be especially beneficial for integrated devices when the handgrip of the invention is a part of the entire colonoscope setup.

Figure 2:
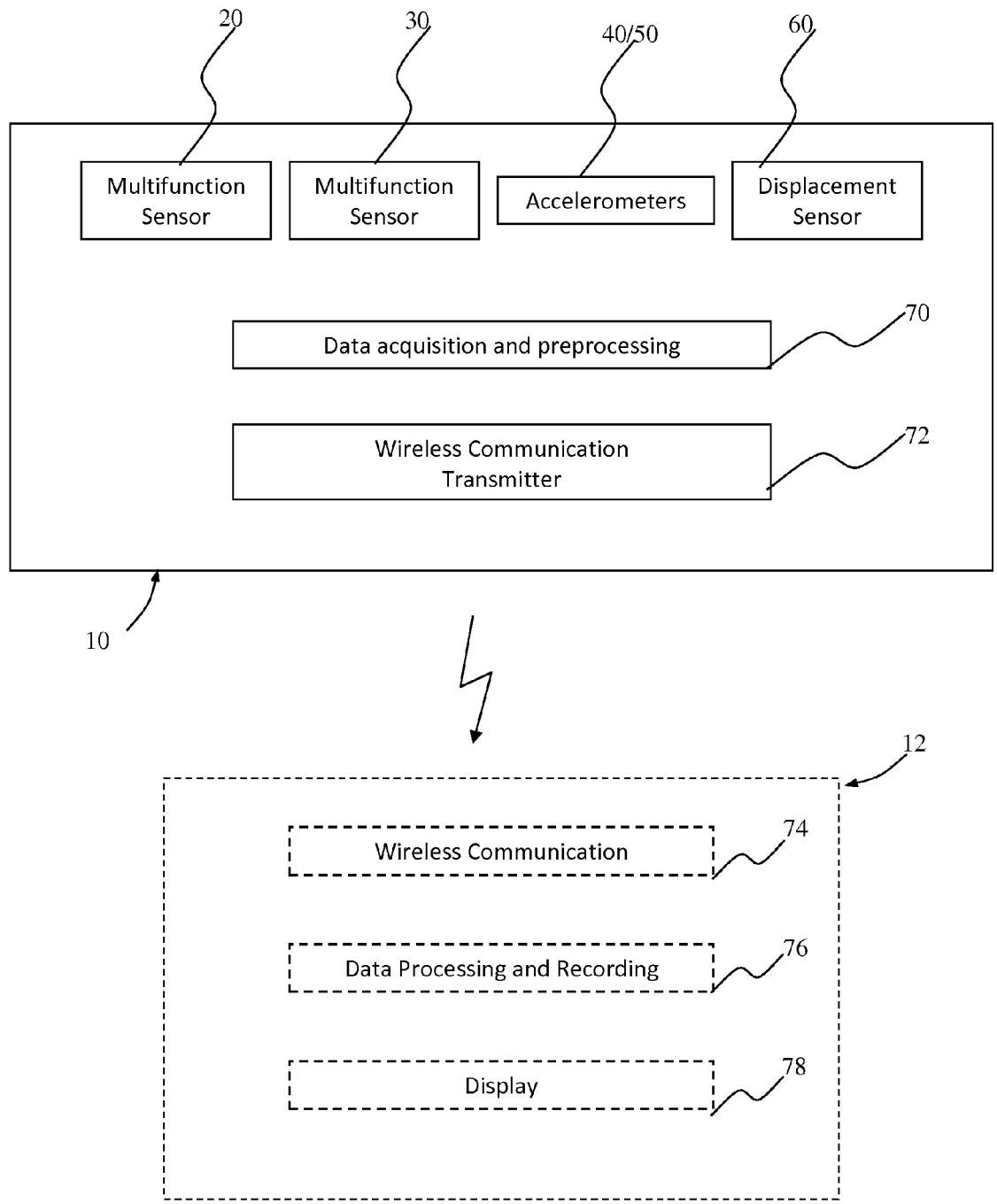
FIG. 2 is a general block-diagram of the components of the handgrip system of the invention.

The block diagram of the handgrip 10 is shown in FIG. 2. A first multifunction force/torque sensor 20 and optionally a second multifunction force/torque sensor 30 may be configured to concurrently measure the forces and torque applied to the colonoscope shaft 80. The linear acceleration data may be provided by linear accelerometer sensor 40 and rotation acceleration data may be provided by rotation acceleration sensor 50. Position and motion of the handgrip relative to colonoscope may be provided by displacement sensor 60.

The concept of a displacement sensor may be similar to that of an optical mouse. The displacement sensor 60 may be configured to track relative shaft motion inside the handgrip—in both directions along the central axis of the device. In embodiments, both axial and radial motion of the shaft may be tracked by the displacement sensor 60.

Together these sensors allow for a comprehensive characterization of the applied forces and torque, and the resulting motions of the colonoscope shaft 80. The data acquisition and preprocessing unit 70 is employed for data acquisition and preprocessing. The handgrip wireless communication transmitter 72 provides data transmission to the electronic unit 12 through wireless communication receiver 74 for further data processing in the data processing and recording module 76. The results may be displayed on the display 78.

The linear and rotation acceleration sensors 40 and 50 may include a combination of accelerometers, magnetometers, and gyroscopes (linear and rotational) as described in US Pat. No. 8,033,991. The purpose of the linear acceleration sensor 40 is to measure the linear acceleration of the handgrip motion along the colonoscope shaft axis. The direction of the linear acceleration is parallel with the direction of the axial force applied to the colonoscope shaft 80 which may be measured as the force component of the multifunction force/torque sensors 20 and 30. The direction of the rotational acceleration coincides with the applied torque which may be measured as the torque component of the multifunction force/torque sensors 20 and 30.

The linear and rotational accelerations may be acquired either directly from or calculated using acquired signals of linear and rotational acceleration sensors 40 and 50, as well as from the displacement sensor 60 using different approaches. One of the possible solutions for the calculation of the linear acceleration may comprise the steps of:
 a) measuring the elevation, rotation, and azimuth angles of the handgrip 10 relative to the gravity and magnetic vectors of the Earth,
 b) measuring the three dimensional acceleration vector by a three-axis acceleration sensor 40/50,
 c) calculating the three dimensional acceleration vector produced by displacement of the handgrip 10 by means of subtraction of the gravity vector from the three dimensional acceleration vector of step (b),
 d) calculating a projection of the three dimensional acceleration vector calculated in step (c) to the central axis of the handgrip 10, or
 e) detecting the displacement of the handgrip 10 along the colonoscope shaft 80 by sensor 60.

In embodiments, angular acceleration calculation may comprise the steps of:
 a) measuring the elevation, rotation, and azimuth angles of the handgrip 10 relative to the gravity and magnetic vectors of the Earth,
 b) measuring the three dimensional rotational accelerations using for example rotational gyroscopes,
 c) calculating the rotational acceleration around the central axis from the three dimensional accelerations taking into account the contribution of the gravity vector of the Earth, or
 d) detecting the rotation of the handgrip 10 around the colonoscope shaft 80 by sensor 60.

Importantly, knowing both the linear force and the linear acceleration (or linear repositioning), allows a more comprehensive characterization of the colonoscope shaft 80 push/pull manipulations. Knowing both the torque and angular acceleration (or rotational repositioning), allows a more comprehensive characterization of the colonoscope rotational manipulations. Furthermore, knowing the lateral forces allows a comprehensive characterization of the inadequate endoscope manipulations. This data allows the recognition of an encountered obstacle and the characterization of the way in which a medical practitioner moves the colonoscope shaft to overcome the obstacle and advance the shaft forward. Such an obstacle may be an obstruction or a turn in the colon anatomy. The ratio of the force to the linear acceleration characterizes tissue resistance to the push/pull motions. The ratio of torque to the rotational acceleration characterizes the rotational resistance between the colonoscope shaft and the tissue.

Additionally, the acceleration data of acceleration sensors 40 and 50 may be used for calculating the motion speed of the handgrip 10 as well as the positioning changes in the colonoscope shaft 80 during colonoscope manipulation.

Figure 3A:
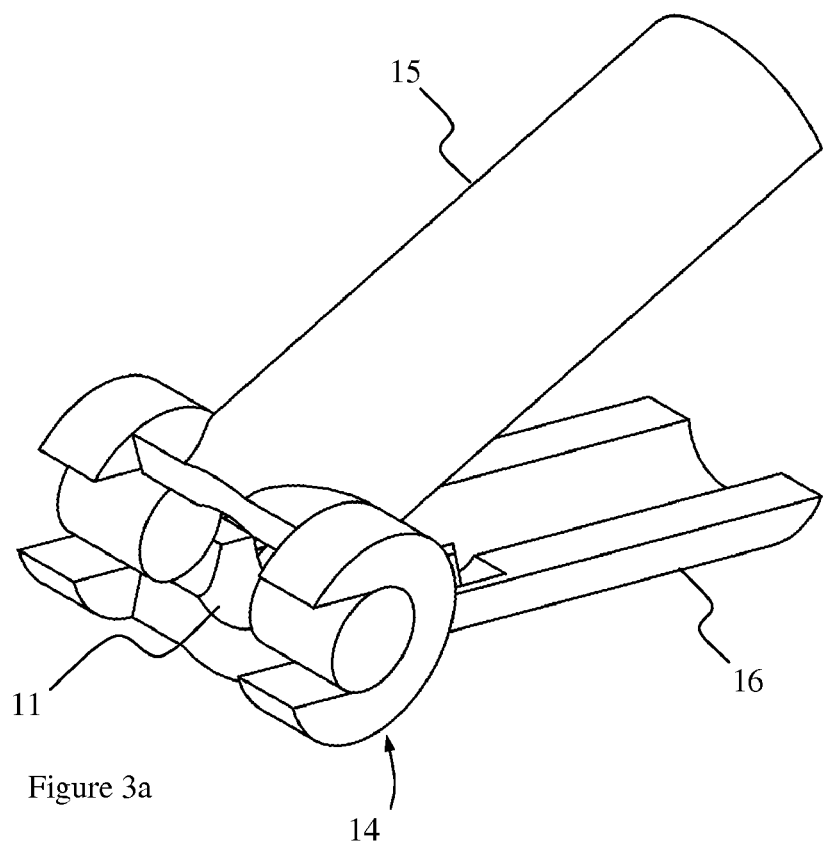
FIG. 3a shows the handgrip in its open "released" state when it is disengaged from the colonoscope shaft.
Figure 3B:
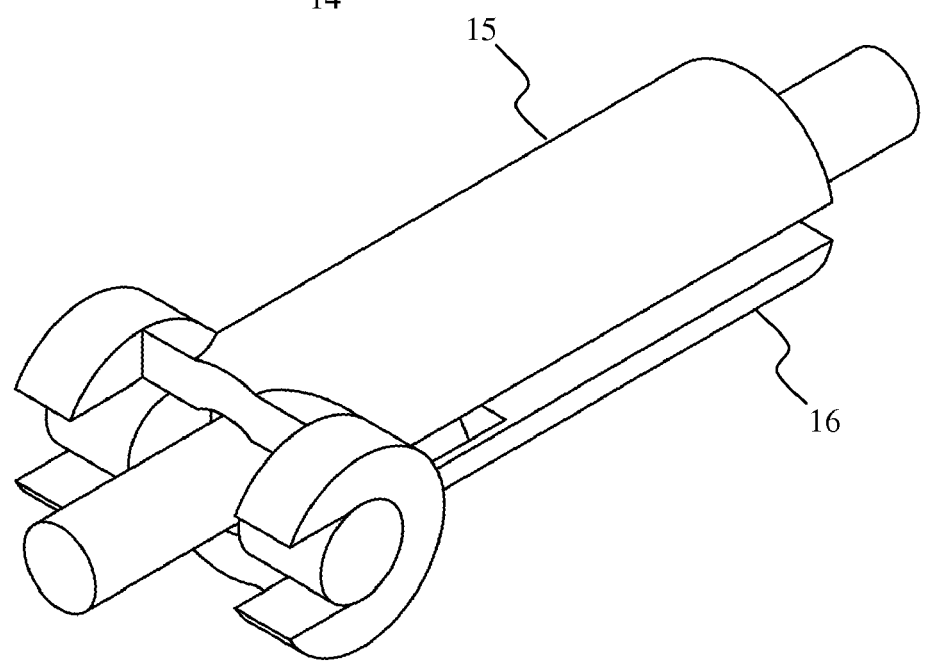
FIG. 3b shows the handgrip of the invention in its closed "engaged" state when the colonoscope shaft is gripped between the handles of the handgrip.
Figure 4:
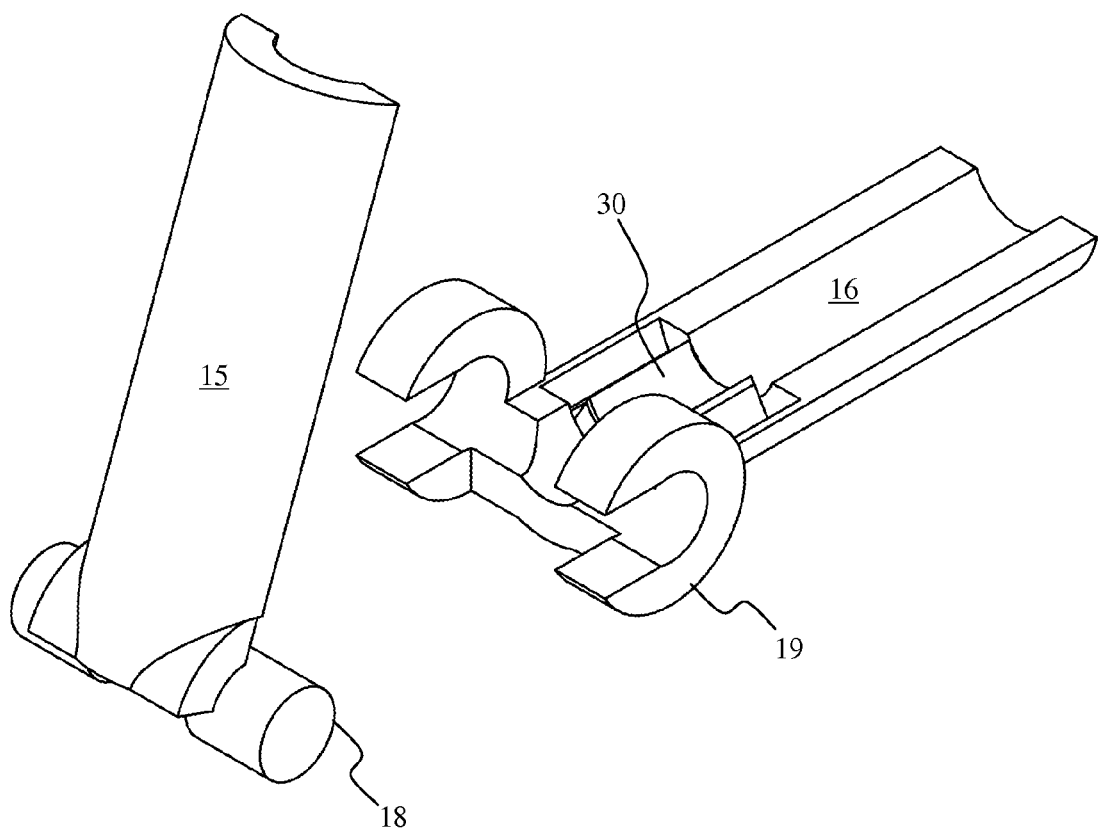
FIG. 4 shows an exploded view of the handgrip showing two separated handles thereof.
Figure 5A:
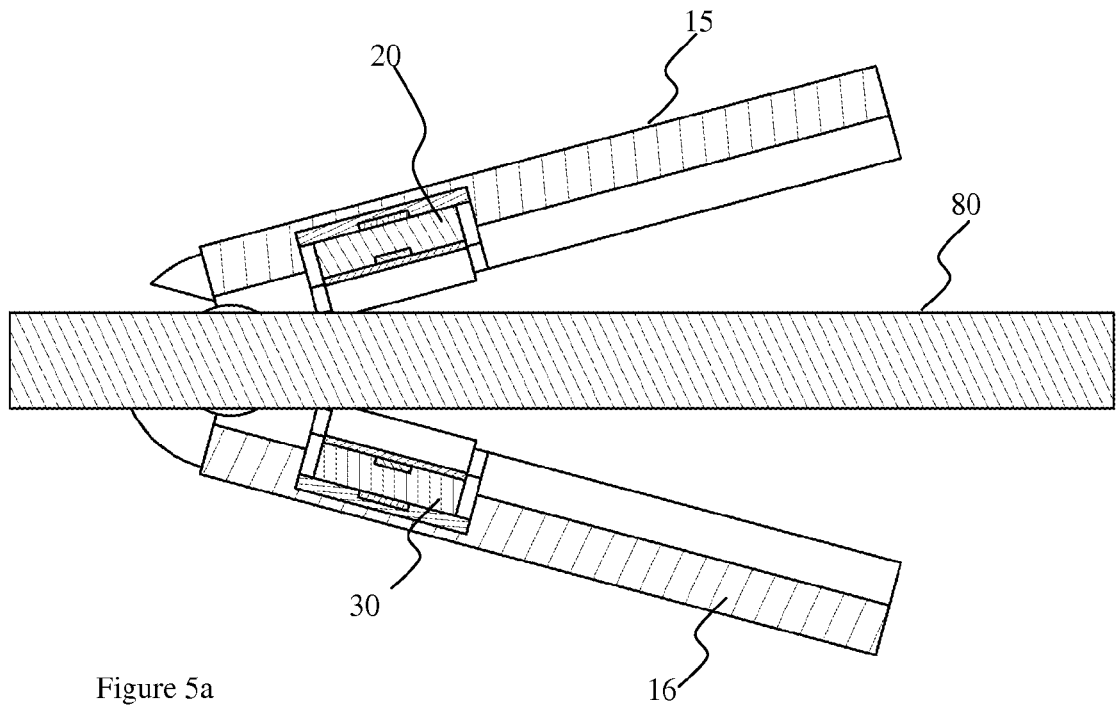
FIGS. 5a and 5b shows cross-sectional views of the same as in FIGS. 3a and 3b.
Figure 5B:
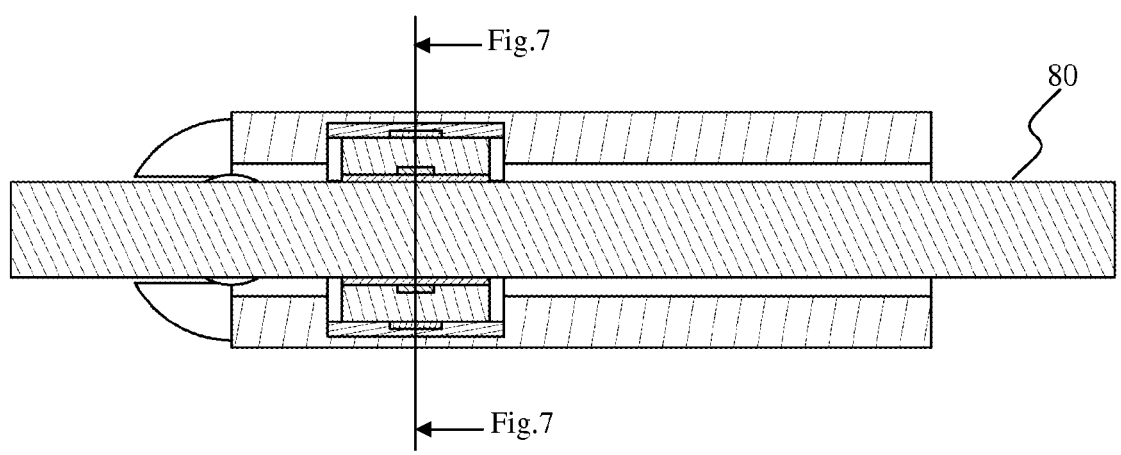

The design of the handgrip 10 of the invention will now be described in more detail. One embodiment of the handgrip 10 is shown in greater detail in FIGS. 3-5. The handgrip 10 comprises a hinge 14 and a clutch formed by a first handle 15 and a second handle 16 extending therefrom. The first handle 15 includes a rod 18 of the cylindrical hinge 14. The second handle 16 includes a ring 19 of the cylindrical hinge 14. The ring 19 may be open for a snap connection as shown in the figures or it may be closed. The advantage of an open ring design is the ability to separate the two parts of the handgrip for cleaning and disinfecting between the procedures. The hinge 14 includes a central opening 11 which allows passage of the colonoscope shaft 80 through the center of the hinge. In embodiments, there may be one or two multifunction force/torque sensors. In case where the handgrip of the invention includes only one multifunction sensor, it may be positioned opposite a resilient gripping member of the same design but lacking the magnetic sensing capability. In other embodiments, the multifunction force/torque sensors 20 and 30 may be attached to the handles 15 and 16, respectively and may be positioned symmetrically opposite each other on both sides of the colonoscope shaft.

The action of engaging the handgrip 10 with the shaft 80 includes bringing two handles 15 and 16 together by squeezing it with one hand which leads to the gripping of the shaft 80 by the multifunction sensors 20 and 30. As the squeezing force is applied at the location further away from the hinge 14 than the location of the multifunction sensors 20 and 30, there is a strong mechanical leverage provided by the design of the handgrip of the invention allowing confident grabbing of the colonoscope shaft 80 with minimum force applied to the handles 15 and 16—even in circumstances of a lubricant being applied to the colonoscope shaft during the procedure. In embodiments, the length of the handles is selected to be at least 3 times greater than the distance between the multifunction sensor and the hinge providing at least threefold gripping force amplification through mechanical leverage.

Additional sensors 40, 50, 60 and other electronics as described above may be contained within the bodies of the handles 15 and 16, in particular near the hand grip regions. In embodiments, a cable may be provided between the two handles to assure electrical communication between various elements of the handgrip 10 (not shown). In other embodiments, such electrical communication may be provided using electrical contacts formed on the respective hinge portions 18 and 19 of the handles 15 and 16 (not shown). In other yet embodiments, the electronic components of each respective handle 15 and 16 may be configured to communicate directly and independently with the computer 12—via wireless or wired way of data transmission.

To ease the manipulation of the handgrip 10, its opening may be assisted by providing elastic bumpers placed symmetrically on both sides of either the handle 15 or the handle 16. The bumpers are compressed when the handles are in a closed "engaged" position and provide for an opening force upon release of the handles 15 and 16. Other spring-loaded release mechanisms and springs may also be used for this purpose as the invention in not limited in this regard.

Figure 6A:
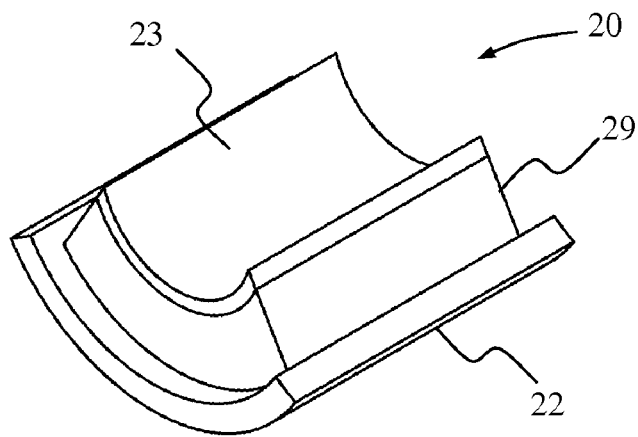
FIGS. 6a and 6b show a general view and a cross-sectional view of the multifunction force/torque sensor of the invention.
Figure 6B:
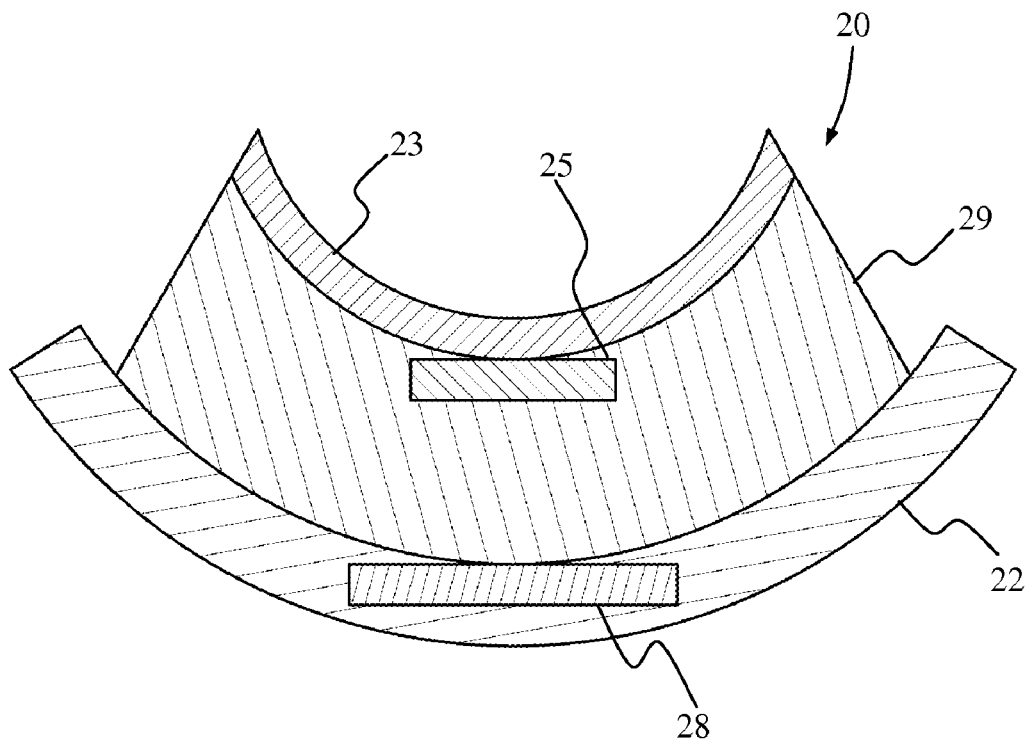
Figure 7:
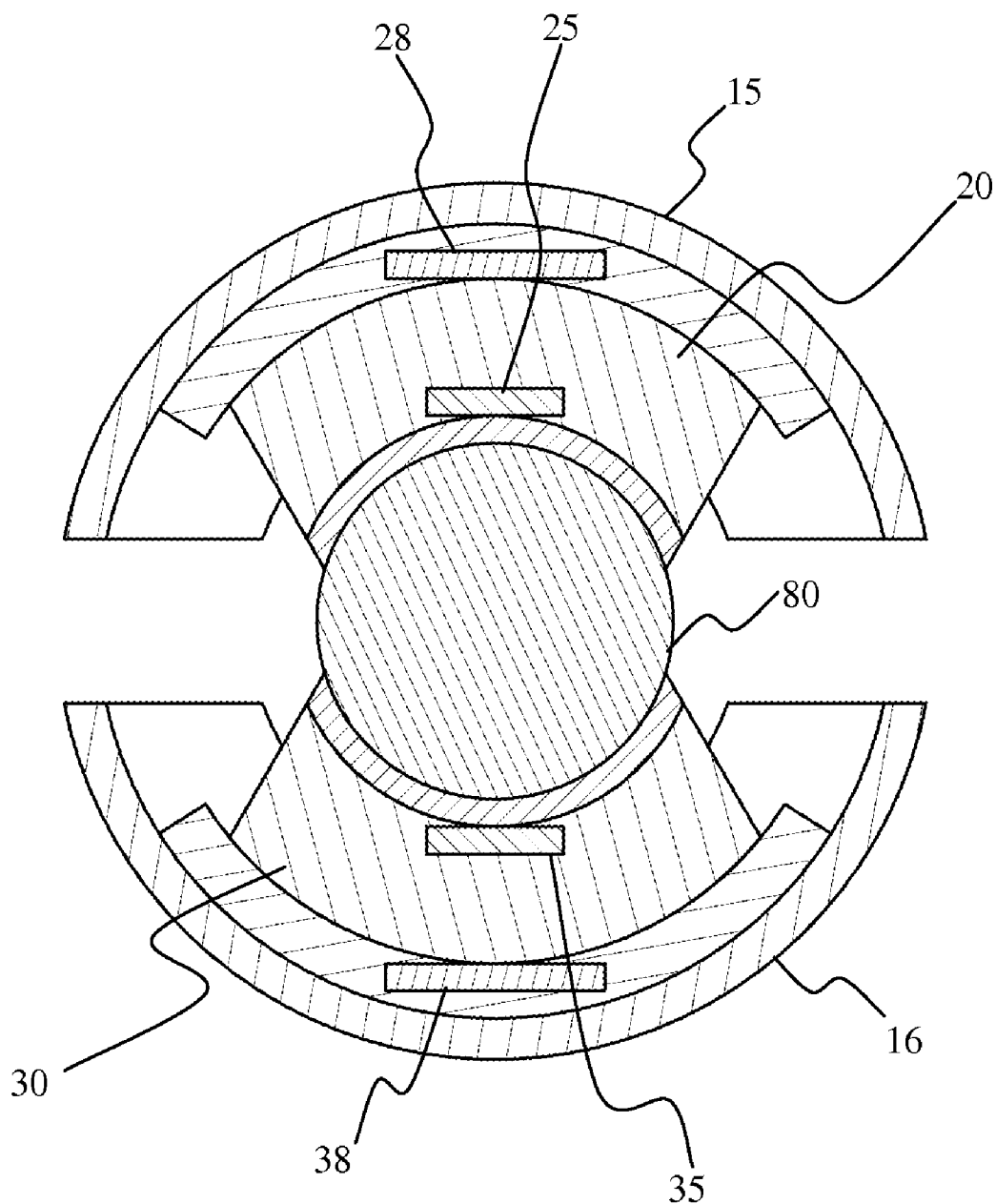
FIG. 7 shows a cross-sectional view of the handgrip of the invention in its "engaged" state over the colonoscope shaft.

A multifunction force/torque sensor 20 is shown in detail and in cross section 26 in FIGS. 6*a* and 6*b* respectively. The multifunction sensor 20 may have a semi-round rigid base 22 which provides a structural support for the sensor 20. In embodiments, the base 22 may be attached to or embedded into the respective handgrip handle. In other embodiments, the base 22 may be inserted into a handgrip handle as a socket connection as the invention is not limited in this regard.

The multifunction sensor 20 may also include a magnetometer 28 located at or near the base 22 along with the supporting electronics which are not shown. In embodiments, the magnetometer may be a three-dimensional magnetometer to provide the most comprehensive information for the sensor 20. In embodiments, the magnetometer 28 may include one, two or three one-dimensional magnetometers oriented along mutually orthogonally axis. Importantly, the magnetometer 28 may be selected to measure the magnetic field of the magnet 25 without saturating within the potential volume of magnet displacements.

The multifunction sensor 20 further includes a resilient gripping member 29 made from an elastic material, such as silicone. The material may be selected to provide enough stiffness so as to assure reliable grip of the colonoscope shaft 80 during use. At the same time, the material should exhibit enough deflection to enable detection of the displacement of the magnet 25 by the magnetometer 28. In embodiments, QM 280 silicone produced by Quantum Silicones (Richmond, Va.) may be used to make the resilient gripping member 29. The resilient gripping member 29 may include a non-slip high-friction inner layer 23. In embodiments, the non-slip layer may include a plurality of protrusions extending from its inner surface to further enhance the contact between the handgrip 10 and the colonoscope shaft 80 when both handles 15 and 16 are brought together. In embodiments, the non-slip inner layer 23 may be made to have a curvature of its inner surface to match that of the colonoscope shaft 80.

The multifunction sensor 20 further includes a magnet 25 which may be positioned on or within the resilient gripping member 29. Importantly, the magnet 25 may be located within the sensitivity boundaries of the magnetometer 28. In embodiments, the magnetometer 28 may be located right underneath and in close proximity to the magnet 25. In embodiments, the magnet 25 is selected to have a magnetic field strongly exceeding that of the magnetic field of the Earth. Rare earth magnets may be used for the purposes of the invention allowing the magnet to be small in size. In embodiments, a Neodymium disk having ⅛ of an inch in diameter and 1/32 of an inch in thickness and a surface field of about 3300 Gauss may be used as a magnet 25.

In combination, the magnet 25 and the magnetometer 28 form a sensor allowing tracking of the position of the magnet 25 relative to the position of the magnetometer 28. Since the magnetometer 28 is rigidly attached to the handgrip 10, the sensor 20 allows tracking of the relative displacement of the magnet 25 within the coordinate system of the handgrip 10. As the engaging of the colonoscope shaft 80 with the handgrip 10 is accomplished through compressing the resilient gripping member 29 about the shaft 80, any force or torque applied by the handgrip 10 to the colonoscope shaft 80 will result in a distortion of the shape of the gripping member 29. Such shape distortion will cause slight movement of the magnet 25 which can be detected by the magnetometer 28. Magnetometer signal can therefore be used to assess the degree and direction of the shape distortion of the resilient gripping member 29 and as such will represent forces and torques applied to the colonoscope shaft 80.

In use, the handles 15 and 16 of the handgrip 10 are first placed over the colonoscope shaft 80 and the hinge 14 is assembled. After initialization of the electronics and establishing a wireless connection with the computer 10, the device is ready to use. The magnetometer 28 is activated to detect the neutral position of the magnet 25 when the handgrip is in its unloaded "released" state.

During the colonoscopy procedure, the operator holds the handgrip in one hand and periodically applies hand force to bring the handles 15 and 16 together. That motion causes the hinged handles of the handgrip clutch to apply compression force on two respective multifunction sensors 20 and 30. The sensors 20 and 30 in turn transmit the compression force to the non-slip inner contact layer 23 which is placed in contact with the colonoscope shaft 80. Grip of the colonoscope shaft 80 through the compression of sensors 20 and 30 causes a radial displacement of the magnet 25 in the resilient gripping member 29 bringing it closer to the magnetometer 28. The degree of radial displacement of the magnet 25 is a function of the compression force and therefore the magnetometer 28 may be used to assess whether the minimum compression force has been applied to the colonoscope shaft 80 in order to engage the handgrip therewith.

In embodiments, reaching a predetermined compression threshold may be used to start recording subsequent data from various sensors of the handgrip 10. To save computer memory and not process sensor signals when the handgrip 10 is not engaged with the colonoscope, the system may be programmed to ignore sensor signals at all times except when the compression force exceeds such threshold indicating active colonoscope manipulation using the handgrip of the invention.

Figure 8A:
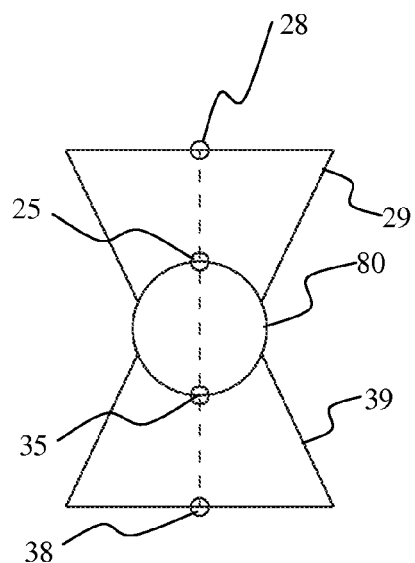
FIGS. 8a through 8e show the operation of the multifunction force/torque sensor for various rotary and linear motions applied to the colonoscope shaft through the handgrip of the invention.

Assuming the handles 15 and 16 are in closed position and the active manipulation of the colonoscope is progressing, reference is now made to FIGS. 8*a* to 8*e* illustrating the principles of operation for the multifunction force/torque sensor 20. FIG. 8*a* shows in cross-section an initial neutral position of the magnet 25 and magnetometer 28 of the first sensor 20 as well as the initial neutral position of the respective magnet 35 and the magnetometer 38 of the second multifunction sensor 30 located diametrically opposite each other.

Figure 8B:
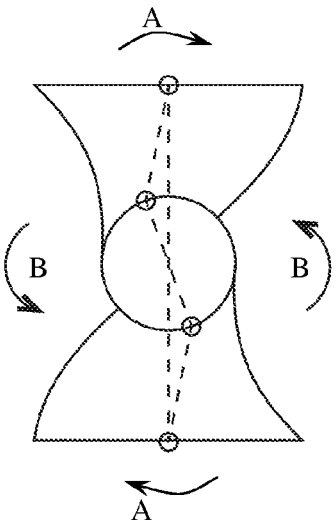

FIG. 8*b* schematically shows a case of rotation of the shaft 80 using the handgrip 10 moved in the direction of the arrows A. Both resilient gripping members 29 and 39 are distorted in the direction of the arrows B and the position of the magnets 25 and 35 is changed. Lateral displacement of the magnets as detected by their respective magnetometers may be used to indicate the torque level applied to the shaft of the colonoscope 80 by the handgrip 10. Note that the lateral displacements of the magnets are recorded in the opposite directions.

Figure 8C:
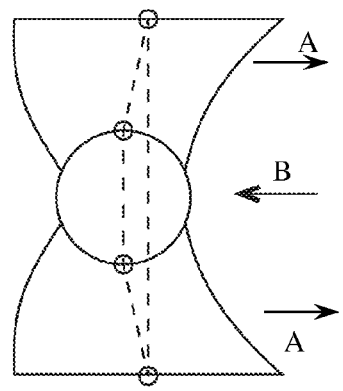

FIG. 8*c* shows a lateral force applied to the shaft 80 by twisting the handgrip in the direction A—in this case lateral displacements of the magnets in the direction B are detected as both happening in the same direction, which is interpreted by the control unit of the system in a manner which is different from the case shown in FIG. 8*a*.

Figure 8D:
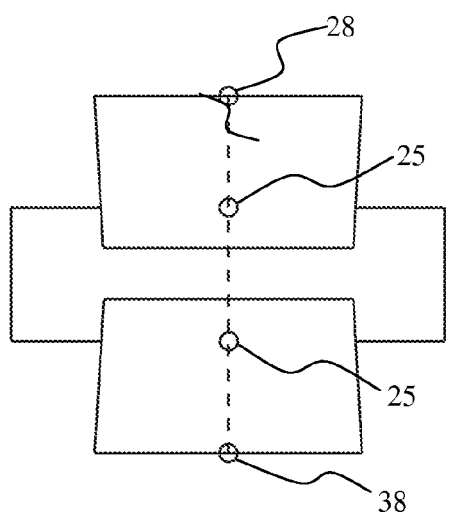
Figure 8E:
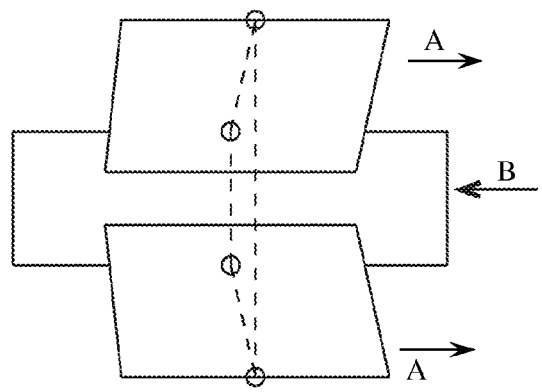

FIG. 8*d* shows schematically a longitudinal section of the neutral position of the sensors 20 and 30 when placed over the colonoscope shaft 80. Illustrated in FIG. 8*e* is the case of applying an axial force along the shaft 80 by pushing the handgrip 10 in the direction of the arrow A causing the magnets 25 and 35 to be displaced in the direction of the arrow B.

in embodiments, an average of two readings from sensor 20 and sensor 30 may be used to detect the axial force applied to the colonoscope shaft 80.

Exact force and torque data may be obtained from sensor signals using specific mathematical equations describing the displacements of a magnet as a function of the dimensions and elastic properties of the resilient gripping member. In embodiments, a simplified method of obtaining this information may be deployed by using a calibration procedure for each of the multifunction force/torque sensors 20. Placing rod through the handgrip and applying predetermined forces and torques thereto allows recording a calibration dataset of values which may be stored with each individual unit. In use, this calibration dataset may be taken into account by the electronic control unit when calculating forces and torques from the signals received from individual sensors.

The herein described subject matter sometimes illustrates different components or elements contained within, or connected with, different other components or elements. It is to be understood that such depicted architectures are merely examples, and that in fact many other architectures may be implemented which achieve the same functionality. For example, a clutch mechanism may be formed by other mechanical arrangements designed to apply a compression force to the colonoscope shaft through the multifunction sensor or sensors. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A handgrip system for measuring forces and torques applied to a shaft of a colonoscope during a colonoscopy procedure, said system comprising:
    a handgrip comprising a first resilient gripping member placed about said colonoscope shaft and a clutch configured to compress said first resilient gripping member to releasably engage said handgrip with said colonoscope shaft,
    a first multifunction force/torque sensor comprising a first magnet positioned on or within said first resilient gripping member and a first magnetometer configured to detect at least an axial displacement of said first magnet from a neutral position thereof in a direction along said colonoscope shaft, said magnetometer is further configured to detect a lateral displacement of said first magnet from the neutral position thereof in a direction tangential to said colonoscope shaft, and
    an electronic control unit configured to determine an axial force applied to said colonoscope shaft using said axial displacement of said first magnet; said electronic control unit is further configured to determine a torque applied to said colonoscope shaft using said lateral displacement of said first magnet.

2. The handgrip system as in claim 1, wherein said handgrip further includes a second resilient gripping member, a second magnet positioned on or within thereof, and a second magnetometer configured to detect at least an axial displacement of said second magnet from a neutral position thereof in a direction along said colonoscope shaft and a lateral displacement of said second magnet from the neutral position thereof in a direction tangential to said colonoscope shaft; said electronic control unit is further configured to determine the axial force applied to said colonoscope shaft using axial displacements of said first and said second magnets; said electronic control unit is further configured to determine said torque applied to said colonoscope shaft using lateral displacements of said first and said second magnets.

3. The handgrip system as in claim 2, wherein said first and said second resilient gripping members with respectively said first and said second magnets are located diametrically opposite each other on both sides of said colonoscope shaft.

4. The handgrip system as in claim 2, wherein said electronic control unit is configured to determine the axial force applied to said colonoscope shaft using an average of said axial displacements of said first and said second magnets; said electronic control unit is further configured to determine said torque applied to said colonoscope shaft using an average of said lateral displacements of said first and said second magnets.

5. The handgrip system as in claim 1, wherein said first magnetometer is further configured to detect a radial displacement of said first magnet from the neutral position thereof in a radial direction orthogonal to said colonoscope shaft, said electronic control unit is configured to determine a compression force applied to said colonoscope shaft using said radial displacement of said first magnet.

6. The handgrip system as in claim 5, wherein said electronic control unit is configured to detect a presence of an engagement state of the handgrip with said colonoscope shaft when said compression force is greater than a predetermined compression threshold; said electronic control unit is further configured to detect a presence of a release state of the handgrip with said colonoscope shaft when said compression force is lower than said predetermined compression threshold.

7. The handgrip as in claim 6, wherein said electronic control unit is configured to collect force and torque data only when said engagement state is present.

8. The handgrip system as in claim 1, wherein said first resilient gripping member includes a non-slip inner contact layer for engaging with said colonoscope shaft upon compression of said first resilient gripping member.

9. The handgrip system as in claim 8, wherein said non-slip inner contact layer includes a plurality of raised protrusions extending from an inner surface thereof.

10. The handgrip system as in claim 1, wherein said first gripping member is made of silicone.

11. The handgrip system as in claim 1, wherein said first magnetometer is a three-axis magnetometer.

12. The handgrip system as in claim 1, wherein said first magnet is a rare earth magnet.

13. The handgrip system as in claim 1 further including a linear accelerometer and a rotational accelerometer.

* * * * *